(12) United States Patent
Manring et al.

(10) Patent No.: US 12,156,718 B2
(45) Date of Patent: Dec. 3, 2024

(54) SYSTEMS AND METHODS TO IMPROVE MANAGEMENT AND MONITORING OF CARDIOVASCULAR DISEASE

(71) Applicant: THE CURATORS OF THE UNIVERSITY OF MISSOURI, Columbia, MO (US)

(72) Inventors: Noah Manring, Columbia, MO (US); Patrice Delafontaine, New Orleans, LA (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 18/215,197

(22) Filed: Jun. 28, 2023

(65) Prior Publication Data

US 2023/0329562 A1  Oct. 19, 2023

Related U.S. Application Data

(63) Continuation of application No. 17/093,550, filed on Nov. 9, 2020.

(Continued)

(51) Int. Cl.
*A61B 5/02*    (2006.01)
*A61B 5/00*    (2006.01)
*A61B 5/021*   (2006.01)
*A61B 5/024*   (2006.01)
*A61B 5/029*   (2006.01)

(Continued)

(52) U.S. Cl.
CPC ...... *A61B 5/02007* (2013.01); *A61B 5/02028* (2013.01); *A61B 5/021* (2013.01); *A61B 5/024* (2013.01); *A61B 5/029* (2013.01); *A61B 5/7278* (2013.01); *A61B 8/065* (2013.01); *A61B 8/0883* (2013.01); *A61B 8/5223* (2013.01); *A61B 8/5261* (2013.01); *G16H 40/67* (2018.01); *G16H 50/30* (2018.01); *A61B 5/0002* (2013.01)

(58) Field of Classification Search
None
See application file for complete search history.

(56) References Cited

U.S. PATENT DOCUMENTS

2014/0121544 A1* 5/2014 Sugo ............... A61B 5/029
600/484

* cited by examiner

*Primary Examiner* — Joel Lamprecht
*Assistant Examiner* — Ashish S Jasani
(74) *Attorney, Agent, or Firm* — STINSON LLP (57) ABSTRACT

The present invention is directed to systems and methods for identifying a cardiovascular disease of a patient. In one embodiment, the method includes obtaining measurements for a diastolic pressure, a systolic pressure, a heartbeat period, a stroke volume, and an ejection period for the patient, and then determining an aortic compliance for the patient based on these measurements. The diastolic pressure, systolic pressure, and heartbeat period are each measured directly from the patient, and the stroke volume and ejection period are each measured from echocardiogram data. In another embodiment, the method includes obtaining measurements for a diastolic pressure and a systolic pressure for the patient, obtaining an estimate of a stroke volume for the patient, and then determining an aortic compliance for the patient based on the diastolic pressure, the systolic pressure, and the stroke volume. These methods may be implemented using a computing device that optionally accesses an electronic medical record to retrieve the relevant parameters.

10 Claims, 6 Drawing Sheets

Related U.S. Application Data

(60) Provisional application No. 62/931,826, filed on Nov. 7, 2019.

(51) Int. Cl.
*A61B 8/06* (2006.01)
*A61B 8/08* (2006.01)
*G16H 40/67* (2018.01)
*G16H 50/30* (2018.01)

SYSTEMS AND METHODS TO IMPROVE MANAGEMENT AND MONITORING OF CARDIOVASCULAR DISEASE

CROSS-REFERENCE TO RELATED APPLICATIONS

This application is a continuation of U.S. Non-Provisional Patent Application Ser. No. 17/093,550 filed on Nov. 9, 2020, which is based on and claims priority to U.S. Provisional Patent Application Ser. No. 62/931,826 filed on Nov. 7, 2019, both of which are incorporated herein by reference in their entireties.

STATEMENT REGARDING FEDERALLY SPONSORED RESEARCH OR DEVELOPMENT

Not applicable.

STATEMENT REGARDING JOINT RESEARCH AGREEMENT

Not applicable.

BACKGROUND OF THE INVENTION

Cardiovascular compliance, which is also referred to as capacitance, is known to be an independent predictor for future cardiovascular events (e.g., coronary heart disease, myocardial infarction, stroke events, and target organ damage) regardless of previous cardiovascular diseases, age, or diabetes. A cardiovascular system with a high capacitance is said to be compliant and soft, while a cardiovascular system with a low capacitance is said to be non-compliant, hard and stiff. Patients with a lower-than-normal cardiovascular compliance are at risk for developing cardiovascular disease and, thus, knowledge of compliance is important.

A crude approximation for total cardiovascular compliance has been used in the past by taking the ratio of the stroke volume of the left ventricle and the pulse pressure within the aorta. However, this method requires a noninvasive estimate of the stroke volume and pulse pressure, and has not been shown to be a significant or independent predictor for mortality. More local measurements of arterial compliance have been assessed using ultrasound methods or magnetic resonance imaging for measuring the deformation of arteries while they undergo pressure pulsations from the heart. However, these methods are time consuming, and have shown their value to be primarily related to pathophysiology, pharmacology, and therapeutics, rather than for epidemiological studies.

The current "gold standard" for assessing arterial compliance has been the use of the carotid-femoral Pulse Wave Velocity (PMV) test. The PWV is determined by simultaneously recording the pressure waveform at two different sites in the arterial tree, namely, the carotid artery in the neck and the femoral artery near the groin. These measurements are typically taken using noninvasive methods of transcutaneous tonometry. The distance between the two arterial segments is then divided by the time delay between the two waveforms. This calculated velocity is called the PWV and is intended to be an indirect measure of the regional compliance between the carotid and femoral arteries within the arterial tree. While the total arterial compliance of the body is of most relevance for assessing health, a measure of the regional compliance between the carotid and femoral arteries is believed to be a good indicator of the total compliance insofar as the compliance of these larger blood vessels tends to dominate the total compliance of the body. It has been deemed that a healthy PWV test is one that produces a result of 6 meters/second to 7 meters/second. A PWV that exceeds 13 meters/second is considered to be a strong predictor of cardiovascular mortality.

As noted above, the PWV is not a direct measure of total cardiovascular compliance, i.e., the units of velocity (length over time) are not the same as the units of compliance/capacitance (volume over pressure). With that said, it is possible to develop an equation using water hammer analysis which shows that the compliance of the fluid conduit is inversely proportional to the square of the PWV and that the compliance increases slightly with mean pressure. The compliance is also directly proportional to the volume of blood in the conduit and so this too must be known with some degree of certainty if the PWV is to be a reasonable surrogate for aortic compliance. Another complicating factor in using the PWV is that the distance between the carotid and femoral arteries is not easy to determine, especially for men with abdominal obesity or women who have a large bust size. Another concern with the PMV test is that it is not a routine measurement that is taken in the clinic or hospital for assessing cardiovascular health. Rather, it is a specialized test that remains primarily within the realm of cardiovascular research.

Thus, there is a need for improved systems and method for assessing aortic compliance in order to improve the management and monitoring of patients with cardiovascular disease.

BRIEF SUMMARY OF THE INVENTION

The present invention is directed to systems and method for assessing aortic compliance in order to improve the management and monitoring of patients with cardiovascular disease.

In one embodiment, a mathematical model for the compliance of the aorta is derived based upon the conservation of mass, which enables aortic compliance to be determined based on five parameters—diastolic pressure, systolic pressure, heartbeat period, stroke volume of the left ventricle, and ejection period. Blood pressure is routinely measured in the clinic to determine the systolic and diastolic pressures of the blood-pressure pulse. The heartbeat period (i.e., heart rate) is also routinely measured in the clinic. The stroke volume and ejection period may be determined from echocardiogram data in order to obtain accurate numbers for a specific patient. Notably, an echocardiogram is more common than a PWV test. The total peripheral resistance may also be determined based on these same five parameters. The aortic compliance and total peripheral resistance are the lumped parameters that describe the ability of the blood vessels to absorb blood pulsations, and to resist the blood flowing from the high-pressure aorta to the low-pressure vena cava.

The above-described method may be modified based on the assumption that the ejection period is equal to one-third of the heartbeat period. In this case, the aortic compliance and total peripheral resistance are determined based on the diastolic pressure, systolic pressure, heartbeat period, and an estimated stroke volume (it is not necessary to obtain the ejection period from an echocardiogram). The stroke volume may be estimated, for example, based on a person's age, height, medical history, weight, and/or previous measurements.

In yet another embodiment, the compliance of the aorta is determined based on the PWV and the mean arterial pressure. The PWV may be measured using known methods for obtaining the carotid-femoral PWV measurement. The mean arterial pressure may be determined based on four parameters—diastolic pressure, systolic pressure, heartbeat period, and ejection period (which may be obtained in the same manner as described above). The method of obtaining the mean arterial pressure may be modified based on the assumption that the ejection period is equal to one-third of the heartbeat period, in which case only the diastolic and systolic pressures are required.

Each of the above methods may be implemented using a computing device that receives the relevant parameters and/or test results (which will vary depending on which method is used), determines the aortic compliance and/or peripheral resistance based on this information, and then presents the aortic compliance and/or peripheral resistance via a user interface to enable a physician or other clinician to identify a cardiovascular disease of the patient. In some embodiments, the computing device accesses an electronic medical record to retrieve the relevant parameters and/or test results.

Various other embodiments and features of the present invention are described in detail below, or will be apparent to one skilled in the art based on the disclosure provided herein, or may be learned from the practice of the invention.

DETAILED DESCRIPTION OF EXEMPLARY EMBODIMENT

The present invention is directed to systems and method for assessing aortic compliance in order to improve the management and monitoring of patients with cardiovascular disease. While the invention will be described in detail below with reference to various exemplary embodiments, it should be understood that the invention is not limited to the specific systems or methodologies of these embodiments. In addition, although the exemplary embodiments are described as embodying several different inventive features, one skilled in the art will appreciate that any one of these features could be implemented without the others in accordance with the invention.

In the present disclosure, references to "one embodiment," "an embodiment," "an exemplary embodiment," or "embodiments" mean that the feature or features being described are included in at least one embodiment of the invention. Separate references to "one embodiment," "an embodiment," "an exemplary embodiment," or "embodiments" in this disclosure do not necessarily refer to the same embodiment and are also not mutually exclusive unless so stated and/or except as will be readily apparent to one skilled in the art from the description. For example, a feature, function, etc. described in one embodiment may also be included in other embodiments, but is not necessarily included. Thus, the present invention can include a variety of combinations and/or integrations of the embodiments described herein.

Generally, the present disclosure describes two different embodiments for assessing aortic compliance: (1) a blood pressure embodiment in which the aortic compliance is based on five parameters (i.e., stroke volume $\Delta V$, ejection period $T_e$, heartbeat period T, diastolic pressure $P_d$, and systolic pressure $P_s$) and (2) a PWV embodiment in which the aortic compliance is based on the PWV and the mean arterial pressure $P_m$. These two embodiments have both been shown to be effective in assessing aortic compliance through in vitro experimentation and, as such, either embodiment may be used depending upon the available data. Provided below is a description of the blood pressure and PWV embodiments, experimentation data for each of these embodiments, and a computing system that may be used to implement these embodiments in a clinical setting.

The disclosure of the blood pressure and PWV embodiments provided below includes numerous symbols that are used to reference certain terms/variables, as shown in Table 1 below:

TABLE 1

| Symbol | Term/Variable |
|---|---|
| a | Area |
| A | local cross-sectional area of the aorta |
| $\overline{A}$ | average cross-sectional area of the aorta |
| $A_0$ | local cross-sectional area of the aorta when the pressure is zero |
| c | wave propagation speed |
| C | total aortic compliance |
| D | outside diameter of the aorta |
| $D_0$ | outside diameter of the aorta when the blood pressure is zero |
| d | inside diameter of the aorta |
| $d_0$ | inside diameter of the aorta when the blood pressure is zero |
| E | modulus of elasticity |
| L | length of the aorta |
| $\hat{n}$ | unit vector pointing outwardly normal from the control surface |
| p | fluid momentum vector in the positive x-direction |
| P | instantaneous blood pressure |
| $P_d$ | diastolic pressure |
| $P_m$ | mean arterial pressure |
| $P_s$ | systolic pressure |
| $P_{1,2}$ | pressures at the two ends of the aorta |
| PWV | pulse wave velocity |
| Q | volumetric flow rate from the left ventricle into the aorta |
| $q_a$ | volumetric flow rate across the aortic valve |
| $q_m$ | volumetric flow rate across the mitral valve |
| R | total peripheral resistance |
| $R^2$ | statistical coefficient-of-determination |
| t | time |
| T | heartbeat period |
| $T_e$ | ejection period of the left ventricle during systole |
| u | fluid-velocity vector in the positive x-direction |
| u | blood velocity within the aorta |
| $\overline{u}$ | average fluid velocity within the control volume |
| V | total blood volume in the aorta |
| $V_0$ | total blood volume in the aorta when the blood pressure is zero |
| w | wall thickness of the aorta |
| x | axial position along the aorta |
| δ | increased inside diameter of the aorta due to pressurization |
| δC | local compliance of the control volume |

TABLE 1-continued

| Symbol | Term/Variable |
|---|---|
| δx | axial length of the control volume |
| ΔP | pulse pressure |
| Δt | transit time for the pressure wave |
| ΔV | stroke volume of the left ventricle |
| ρ | blood density |
| ν | Poisson's ratio |

It should be understood that the above-listed terms/variables may not always be repeated in relation to the symbols used in the disclosure and, thus, the disclosure should be read with reference to the nomenclature provided in Table 1.

I. Blood Pressure Embodiment

Figure 1:
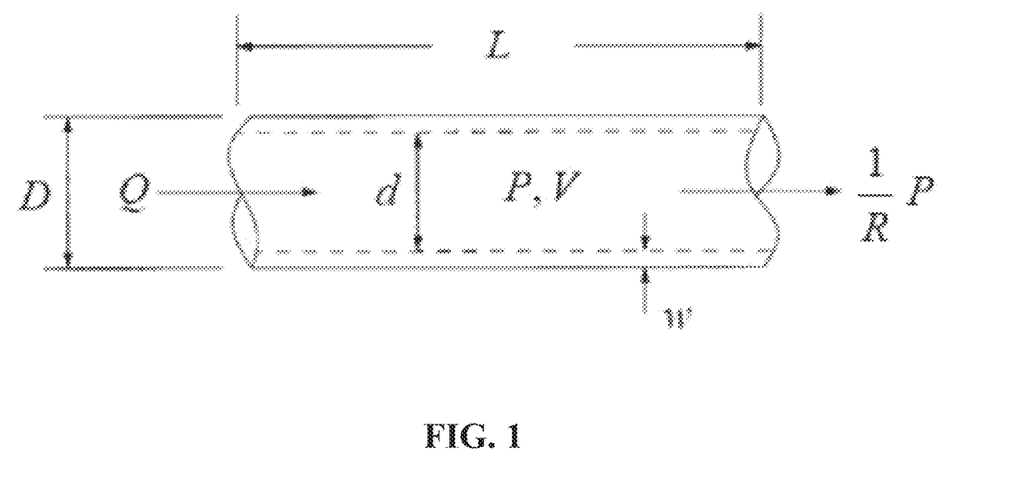
FIG. 1 is a schematic for a section of the abdominal aorta that is used to conduct a blood pressure analysis in accordance with one embodiment of the invention.

FIG. 1 shows a schematic for a section of the abdominal aorta that is used to conduct a blood pressure analysis in accordance with an embodiment of the invention. In FIG. 1, the symbol Q represents the volumetric flow-rate of blood from the left ventricle of the heart which is injected into the aorta during systole. The instantaneous pressure and volume of blood in the aorta are shown by the symbols P and V, respectively. Assuming that the fluid flow through the capillary beds is characterized by a low Reynolds number, the perfusion flow exiting the aorta is shown by the quantity P/R where the symbol R is used to describe the total peripheral resistance of the body. FIG. 1 also shows basic dimensions for the section of the abdominal aorta, including the outside diameter D, the inside diameter d, the wall thickness w, and the section length L.

Using the flow terms that are depicted in FIG. 1, an expression for the conservation of mass may be written as follows:

$$0 = Q - \frac{1}{R}P - \frac{dV}{dt} \qquad (1)$$

where dV/dt is the time rate-of-change of the blood volume within the aorta.

By definition, the capacitance of any fluid volume is given by the following equation:

$$C = \frac{dV}{dP} \qquad (2)$$

Substituting equation (2) into equation (1) and rearranging terms produces the following governing equation for the blood pressure within the abdominal aorta:

$$Q = C\frac{dP}{dt} + \frac{1}{R}P \qquad (3)$$

If the volumetric flow rate of blood coming from the left ventricle Q is modeled in a piecewise fashion in order to approximate the blood flow from the left ventricle during systole and diastole, the following expressions may be obtained:

$$Q = \frac{\Delta V}{T_e} \text{ for } 0 < t < T_e \qquad (4)$$

$$Q = 0 \text{ for } T_e < t < T$$

where ΔV is the stroke volume for the left ventricle during the ejection period $T_e$, and T is the heartbeat period.

Substituting equation (3) into equation (4) and conducting a piecewise integral, the following expressions may be written to describe the instantaneous blood pressure within the aorta:

$$P = \frac{R\Delta V}{T_e} - \left(\frac{R\Delta V}{T_e} - P_d\right)\text{Exp}\left(-\frac{1}{RC}t\right) \text{ for } 0 < t < T_e \qquad (5)$$

$$P = P_s\text{Exp}\left(-\frac{1}{RC}(t - T_e)\right) \text{ for } T_e < t < T$$

Equation (5) may be evaluated when $t=T_e$ and $t=T$ to write the following expressions for systolic pressure $P_s$ and diastolic pressure $P_d$:

$$P_s = \frac{R\Delta V}{T_e}\frac{1 - \text{Exp}\left(-\frac{1}{RC}T_e\right)}{1 - \text{Exp}\left(-\frac{1}{RC}T\right)} \qquad (6)$$

$$P_d = \frac{R\Delta V}{T_e}\frac{1 - \text{Exp}\left(\frac{1}{RC}T_e\right)}{1 - \text{Exp}\left(\frac{1}{RC}T\right)} \qquad (7)$$

Systolic and diastolic pressures are known health markers for hypertensive patients, and equations (6) and (7) show that these pressures are determined by five parameters: total cardiovascular capacitance C, total peripheral resistance R, left-ventricle stroke volume ΔV, heartbeat period T, and ejection period $T_e$.

The mean arterial pressure $P_m$ may be determined by taking the integral average of the solution to equation (3) over the duration of a single heartbeat, which may be expressed as follows:

$$P_m = \frac{1}{T}\int_0^T P dt = P_d \frac{T_e}{T} \frac{1 - (P_s/P_d)^{\frac{T}{T-T_e}}}{1 - (P_s/P_d)^{\frac{T_e}{T-T_e}}} = \frac{R\Delta V}{T} \qquad (8)$$

where ΔV/T is the cardiac output. Equation (8) shows that the mean arterial pressure is equal to the cardiac output ΔV/T multiplied by the total peripheral resistance R.

A simplified form of equation (8) may be written for a healthy ejection period equal to one-third of the heartbeat period. Substituting $T_e=T/3$ into equation (8), the mean arterial pressure $P_m$ may be expressed as follows:

$$P_m = \frac{P_s + P_d + \sqrt{P_s P_d}}{3} \qquad (9)$$

Equation (9) may be used to obtain an approximation for the mean arterial pressure when the ejection period is unknown.

It should be noted that equation (9) predicts a slightly higher mean arterial pressure compared to the "33% formula" commonly used in the clinic and given by $P_m=P_d+$ $(P_s-P_d)/3$. This difference is due to the rectangular flow model in equation (4). Thus, for a healthy blood pressure of $P_s=120$ mm-Hg and $P_d=80$ mm-Hg, it may be shown that the mean arterial pressure calculated using equation (9) is 6.4% higher than the mean arterial pressure calculated using the "33% formula."

The pulse pressure $\Delta P$ is defined as the difference between the systolic and diastolic pressures (which may be calculated from equations (6) and (7), respectively), as follows:

$$\Delta P = P_s - P_d \qquad (10)$$

The pulse pressure is often used to provide a qualitative assessment for aortic compliance. A large pulse pressure is considered an indicator for low compliance and high aortic stiffness.

The aortic compliance C and peripheral resistance R may be separately determined using the systolic and diastolic pressures (which may be calculated from equations (6) and (7), respectively) and the mean arterial pressure (which may be calculated from equation (8)), as follows:

$$C = \frac{\Delta V}{P_m} \frac{T-T_e}{T} \frac{1}{\ln(P_s/P_d)} = \frac{\Delta V}{P_d} \frac{T-T_e}{T} \frac{1}{\ln(P_s/P_d)} \frac{1-(P_s/P_d)^{\frac{T_e}{T-T_e}}}{1-(P_s/P_d)^{\frac{T}{T-T_e}}} \qquad (11)$$

$$R = \frac{P_m T}{\Delta V} \frac{P_d T_e}{\Delta V} \frac{1-(P_s/P_d)^{\frac{T}{T-T_e}}}{1-(P_s/P_d)^{\frac{T_e}{T-T_e}}} \qquad (12)$$

With reference to equations (11) and (12), it is important to note that the aortic compliance C and peripheral resistance R may be determined with knowledge of five parameters: stroke volume $\Delta V$, ejection period $T_e$, heartbeat period T, diastolic pressure $P_d$, and systolic pressure $P_s$. Three of these parameters—heartbeat period T, diastolic pressure $P_d$, and systolic pressure $P_s$—are routinely measured in a doctor's office. The other two parameters—stroke volume $\Delta V$ and ejection period $T_e$—may be measured from echocardiogram data. Thus, all five parameters are available from a fully exploited echocardiogram examination in a hospital, clinic or other healthcare setting. Equation (11) also shows that the aortic compliance C manifests itself as a highly nonlinear combination of these five parameters.

As an example, for a patient with a resting heart rate of 70 bpm, an ejection period of 0.286 seconds, a stroke volume of 70 mL, and systolic and diastolic pressures of 120 mm-Hg over 80 mm-Hg, respectively, it may be calculated from equation (9) that the patient has a healthy aortic compliance of 1.159 mL/mm-Hg. For the same individual, it may be calculated from equation (10) that the patient has a healthy peripheral resistance of 1.216 mm-Hg-s/mL.

As noted above, equation (9) is a simplified form of equation (8) that may be used in cases where a healthy ejection period is equal to one-third of the heartbeat period. Substituting $T_e=T/3$ into equations (11) and (12), the aortic compliance C and peripheral resistance R may be written as follows:

$$C = \frac{\Delta V}{P_s + P_d + \sqrt{P_s P_d}} \frac{2}{\ln(P_s/P_d)} \qquad (13)$$

$$R = \frac{P_s + P_d + \sqrt{P_s P_d}}{3} \frac{T}{\Delta V} \qquad (14)$$

Equations (13) and (14) may be used to estimate the aortic compliance C and peripheral resistance R when the ejection period $T_e$ is unknown. It can be appreciated that an estimate for the stroke volume $\Delta V$ will also be needed for these calculations. In one embodiment, the stroke volume $\Delta V$ is estimated based on a person's age, height, medical history, weight, and/or previous measurements.

As shown in equation (2), the aortic compliance C for the section of the abdominal aorta shown in FIG. 1 is given by the derivative of the blood volume V with respect to the blood pressure P. Using the geometry of FIG. 1, the blood volume of the aortic section is given by the following equation:

$$V = \frac{\pi}{4} d^2 L \qquad (15)$$

As the aorta is pressurized, the inside diameter d increases as follows:

$$d = d_0 + \delta \qquad (16)$$

where $d_0$ is the inside diameter of the aorta when the blood pressure is zero, and $\delta$ is the increased diameter due to pressurization of the vessel.

It is known that the increased diameter for a thick-wall pressure vessel without capped ends is given by the following equation:

$$\delta = d_0 \frac{P}{E}\left(\frac{D_0^2 + d_0^2}{D_0^2 - d_0^2} + v\right) \qquad (17)$$

It should be noted that thick-wall pressure vessel calculations are also valid for thin-wall pressure vessels. In equation (17), P is the fluid pressure within the vessel, E is the modulus of elasticity for the vessel material, v is Poisson's ratio for the vessel material, and $D_o$ is the outside diameter of the pressure vessel when the pressure is zero. By substituting equations (15) and (16) into equation (17) and taking the derivative of the volume with respect to pressure, the following expression may be written to describe the aortic compliance of the aortic section shown in FIG. 1:

$$C = \frac{\pi L d_0^2}{2E}\left(\frac{D_0^2 + d_0^2}{D_0^2 - d_0^2} + v\right) \qquad (18)$$

In equation (18), the pressure-dependence of the aortic compliance has been neglected due to its small size.

II. Pulse-Wave Velocity (PWV) Embodiment

Figure 2:
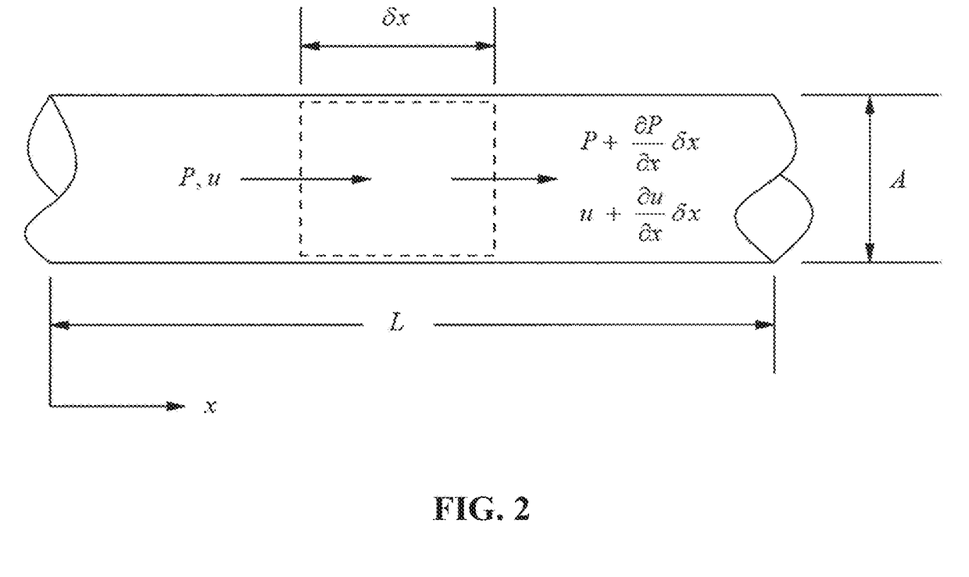
FIG. 2 is a schematic for an infinitesimal control volume within a segment of an aorta that is used to conduct a pulse-wave velocity (PWV) analysis in accordance with an embodiment of the invention.

FIG. 2 shows a schematic for an infinitesimal control volume within a segment of an aorta that is used to conduct a pulse-wave velocity (PWV) analysis in accordance with an embodiment of the invention. The dashed line indicates the control volume that has a length shown by the symbol $\delta x$. The local pressure and blood velocity within the aorta are given by the symbols P and u, respectively. The local cross-sectional area of the aorta is shown by the symbol A and the total length of the aorta segment is given by the symbol L. The aorta is a type of a hydraulic transmission line where the pressure varies as a function of time t and location in the longitudinal direction x. The wave equation for the pressure within the transmission line is known to exist in the following form:

$$\frac{\partial^2 P}{\partial t^2} = c^2 \frac{\partial^2 P}{\partial x^2} \tag{19}$$

where c is the propagation speed of the pressure wave within the aorta, which is also known as the pulse-wave velocity (PWV). As described below, it is possible to derive an expression for PMV as a function of physically relevant parameters.

In the analysis described below, the following assumptions are made: (1) the blood will be considered incompressible, while the aorta will be considered elastic; (2) the inflow of momentum across the control volume boundary is negligible compared to the time rate-of-change of momentum within the control volume, and will thus be neglected; (3) the viscous shear stress at the inside wall of the aorta will be neglected; (4) the blood pressure varies with time t and in the longitudinal x-direction, but not in the radial direction; (5) the cross-sectional area of the aorta varies with time and in the longitudinal x-direction due to the elasticity of the vessel and the local pressure; and (6) quadratically small terms throughout the analysis will be neglected.

Using the Reynolds transport theorem, the conservation of mass for the control volume shown in FIG. 1 is given by the following equation:

$$0 = \frac{\partial}{\partial t} \int_{cv} \rho dv + \int_{cs} \rho(u \cdot \hat{n}) da \tag{20}$$

where $\rho$ is the fluid density, dv is an infinitesimally small volume of fluid, u is the blood velocity vector, and $\hat{n}$ is a unit vector that points normally outward from the control surface across which blood is passing. The first term on the right-hand side of equation (20) represents the time rate-of-change of mass within the control volume, and the second term on the right-hand side of equation (20) represents the inflow of mass across the control volume boundary.

If the blood is treated as an incompressible fluid, the fluid density in equation (20) may be canceled from the expression resulting in the following equation for the conservation of mass:

$$0 = \frac{\partial}{\partial t} \int_{cv} dv + \int_{cs} (u \cdot \hat{n}) da \tag{21}$$

The first term on the right-hand side of equation (21) may be expressed as follows:

$$\frac{\partial}{\partial t} \int_{cv} dv = \frac{\partial}{\partial t} (\overline{A} \delta x) = \frac{\partial A}{\partial t} \delta x \tag{22}$$

When the quadratically small terms in equation (22) are neglected, the average cross-sectional area of the control volume may be expressed as follows:

$$\overline{A} = \frac{1}{2}\left(A + A + \frac{\partial A}{\partial x}\delta x\right) \tag{23}$$

The second term on the right-hand side of equation (21) may be expressed as follows:

$$\int_{cs} (u \cdot \hat{n}) da = -uA + \left(u + \frac{\partial u}{\partial x}\delta x\right)\left(A + \frac{\partial A}{\partial x}\delta x\right) \tag{24}$$

$$= -uA + uA + A\frac{\partial u}{\partial x}\delta x + u\frac{\partial A}{\partial x}\delta x + \frac{\partial u}{\partial x}\frac{\partial A}{\partial x}\delta x^2$$

Neglecting quadratically small terms, equation (24) may be simplified as follows:

$$\int_{cs} (u \cdot \hat{n}) da = \frac{\partial (Au)}{\partial x}\delta x = \frac{\partial Q}{\partial x}\delta x \tag{25}$$

where A times u is equal to the volumetric flow rate Q.

Substituting equations (22) and (25) into equation (21) produces the following expression for the conservation of mass:

$$0 = \frac{\partial A}{\partial t} + \frac{\partial Q}{\partial x} \tag{26}$$

where the axial length of the control volume $\delta x$ has canceled out. It will be seen that equation (26) will be used to develop the pressure-wave equation for the aorta.

Using the Reynolds transport theorem, the conservation of momentum for the control volume shown in FIG. 1 is given by the following equation:

$$\frac{Dp}{Dt} = \frac{\partial}{\partial t} \int_{cv} \rho u dv + \int_{cs} \rho u(u \cdot \hat{n}) da \tag{27}$$

where Dp/Dt is the material derivative of the fluid momentum vector p. The first term on the right-hand side of equation (27) represents the time rate-of-change of momentum within the control volume, and the second term on the right-hand side of equation (27) represents the inflow of momentum across the control volume boundary.

With respect to the blood-pressure problem within the aorta, dimensional analysis may be used to show that the inflow of momentum across the control volume boundary is at least one order of magnitude smaller than the time rate-of-change of momentum within the control volume. For this reason, the second term on the right-hand side of equation (27) will be neglected and the conservation of momentum will be written as follows:

$$\frac{Dp}{Dt} = \frac{\partial}{\partial t} \int_{cv} \rho u dv \tag{28}$$

According to Newton's second law, the time rate-of-change for the fluid moment must be equal to the forces that are acting on the surfaces of the control volume. If we neglect shear stress at the inside wall of the aorta and only consider the pressures acting to push the control volume in the positive x-direction, the left-hand side of equation (28) may be written as follows:

$$\frac{Dp}{Dt} = PA - \left(P + \frac{\partial P}{\partial x}\delta x\right)\left(A + \frac{\partial A}{\partial x}\delta x\right) \tag{29}$$

$$= PA - PA - A\frac{\partial P}{\partial x}\delta x - P\frac{\partial A}{\partial x}\delta x - \frac{\partial P}{\partial x}\frac{\partial A}{\partial x}\delta x^2$$

Neglecting quadratically small terms produces the following result for the time rate-of-change for the fluid momentum within the aorta:

$$\frac{Dp}{Dt} = -\frac{\partial(PA)}{\partial x}\delta x \qquad (30)$$

where the vector direction of this result is in the positive x-direction.

It should be noted that previous developments for the PWV equation treat the cross-sectional area A as a constant rather than considering this parameter to vary with respect to x. This is inconsistent with the conservation-of-mass equation presented in equation (26). If the cross-sectional area A is assumed to be independent of x, the final PWV result will be independent of pressure and a significant physical contributor will be lost.

If the fluid density is considered to be constant, and the fluid velocity within the control volume is assumed to be uniform and average in the positive x-direction, the time rate-of-change of the fluid momentum within the control volume may be written as follows:

$$\frac{\partial}{\partial t}\int_{cv}\rho u dv = \frac{\partial}{\partial t}\left(\overline{u}\int_{cv}dv\right) = \rho\frac{\partial}{\partial t}(\overline{u}\overline{A}\delta x) = \rho\frac{\partial Q}{\partial t}\delta x \qquad (31)$$

where the average velocity of the fluid within the control volume is given by the following equation:

$$\overline{u} = \frac{1}{2}\left(u + u + \frac{\partial u}{\partial x}\delta x\right) \qquad (32)$$

and where the average cross-sectional area of the control volume $\overline{A}$ is given in equation (23). It should be noted that quadratically small terms have been neglected in equation (31).

Substituting equations (30) and (31) into equation (28) produces the following expression for the conservation of momentum:

$$0 = \frac{\partial Q}{\partial t} + \frac{1}{\rho}\frac{\partial(PA)}{\partial x} \qquad (33)$$

where, again, the axial length of the control volume $\delta x$ has canceled. This form of the conservation of momentum will be used to develop the pressure-wave equation for the aorta.

Equations (26) and (33) represent the conservation of mass and momentum, respectively, for the blood flowing through the aorta shown in FIG. 1. Taking the derivative of the conservation of mass with respect to time, and the derivative of the conservation of momentum with respect to the spatial coordinate x, the following equations may be written:

$$-\frac{\partial}{\partial t}\left(\frac{\partial Q}{\partial x}\right) = \frac{\partial^2 A}{\partial t^2} \text{ and } -\frac{\partial}{\partial x}\left(\frac{\partial Q}{\partial t}\right) = \frac{1}{\rho}\frac{\partial^2(PA)}{\partial x^2} \qquad (34)$$

Because differentiation is a linear operator, we recognize that:

$$\frac{\partial}{\partial t}\left(\frac{\partial Q}{\partial x}\right) = \frac{\partial}{\partial x}\left(\frac{\partial Q}{\partial t}\right) \qquad (35)$$

Using equations (34) and (35), the wave equation for the blood flow problem may be written as follows:

$$\rho\frac{\partial^2 A}{\partial t^2} = \frac{\partial^2(PA)}{\partial x^2} \qquad (36)$$

This is the basic form of the wave equation that will be further developed below using a constitutive model for the cross-sectional area A as a function of blood pressure P.

Equation (36) shows that the wave equation is dependent upon the local cross-sectional area A. Using the definition for volumetric compliance, it may be shown that this area is given by the following equation:

$$A = A_o + \frac{\delta C}{\delta x}P \qquad (37)$$

where $A_o$ is the local cross-sectional area when the pressure is zero, $\delta C$ is the local compliance, and $\delta x$ is the length of the local control volume shown in FIG. 1. By substituting equation (37) into equation (36) and neglecting small terms, the wave equation may be written as follows:

$$\frac{\partial^2 P}{\partial t^2} = c^2\frac{\partial^2 P}{\partial x^2} \text{ where } c^2 = \frac{1}{\rho}\left(A_o\frac{\delta x}{\delta C} + 2P\right) \qquad (38)$$

In equation (38), c is the propagation speed of the pressure wave within the aorta, which is also equal to the PWV.

The wave equation presented in equation (38) has been developed to describe the blood pressure at a specific time and location within the aorta. By rearranging terms in equation (38), the local compliance within the aorta may be expressed as follows:

$$\delta C = \frac{A_o}{\rho c^2 - 2P}\delta x \qquad (39)$$

Using this form, we may consider the average or overall compliance of the aorta to be the following:

$$C = \frac{V_o}{\rho PWV^2 - 2P_m} \qquad (40)$$

where $V_o$ is the volume of blood in the aorta when the pressure is zero, $P_m$ is the mean arterial pressure, and PWV is the pulse-wave velocity of the blood as measured by known methods for obtaining the carotid-femoral PWV measurement, as described in the Background section above. A significant difference exists between equation (40) and previous known expressions, i.e., equation (40) contains a pressure term that has not been included in previous results. This applied pressure to the fluid is dimensionally significant if $2 P_m/(\rho PWV^2)$ is greater than $1/10$ as demonstrated herein.

For a typical adult, the cardiovascular system has about 5 liters of blood and 7% of this blood is contained in the aorta. This means that the nominal blood volume in the aorta is 350 milliliters. The density of blood is 1060 kilograms/meter$^3$ (slightly more than water) and a healthy mean arterial pressure is 100 mm-Hg. Furthermore, a healthy PWV is given by 8 meters/second. Using these parameters with equation (40), it may be shown that a healthy aortic compliance is given by 1.133 mL/mm-Hg, which is similar to the healthy compliance that was calculated using the blood-pressure model presented in equation (11). If the mean arterial pressure is neglected in equation (40), the aortic compliance will be calculated as 0.688 ml/mm-Hg, which is 39% lower than the expected compliance. Thus, the pressure dependency of equation (40) is important and provides a more accurate result than previous known expressions.

III. In Vitro Experiments

Figure 3:
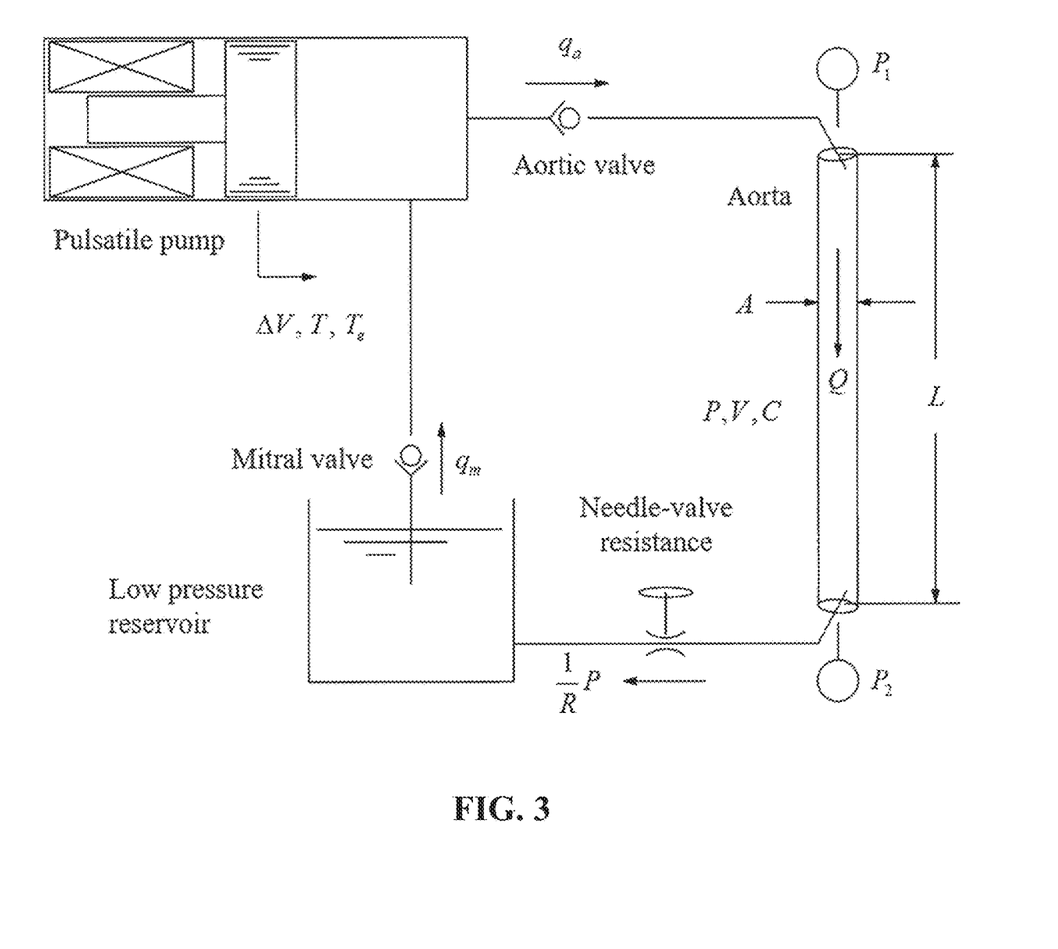
FIG. 3 is a schematic for an experimental setup used to perform in vitro experiments in relation to the blood pressure and PWV embodiments of the invention.

FIG. 3 shows a schematic for an experimental setup that was used to perform in vitro experiments in relation to the blood pressure and PWV embodiments of the invention. In this setup, the left ventricle of the heart is simulated by a pulsatile pump available from BDC Laboratories of Wheat Ridge, CO. This pump is actuated electromagnetically with an ability to deliver a programed flow-pulse that is characterized by a specific stroke volume $\Delta V$, heartbeat period T, and ejection period Te. The aortic valve and the mitral valve are simulated by check valves, which allow flow in only one direction as shown by the symbols $q_a$ and $q_m$, respectively. The aorta model is shown in FIG. 3 as a straight tube of length L and a nominal cross-sectional area given by A. The volume of fluid within the aorta is shown by V. A needle valve is used to adjust the mean arterial pressure within the aorta, and the flow rate across this valve is assumed to be of the low Reynolds-number type, being proportional to the pressure drop across the valve P and inversely proportional to the valve resistance R. The valve resistance R mimics the peripheral resistance of the human body. The low-pressure reservoir is used to simulate the venous side of the cardiovascular system. The working fluid in the experiments is water, not a blood-mimicking fluid. In order to measure the PWV, pressure transducers are located in the vicinity of the two ends of the aorta, identified by the symbols $P_1$ at the top of the tube and $P_2$ at the bottom of the tube. The pressure transducers are capable of measuring pressures between −362 and 3878 mm-Hg with an accuracy better than ±2% of reading. The pressure transducers have a frequency response of 1.2 kHz.

The in vitro experiments performed using the setup shown in FIG. 3 used two model aortae. The first aorta was an elastic tube made from silicone rubber, with an inside diameter of 2.54 cm and a wall thickness of 1.4 mm. The length of the tube was 36.5 cm, making the unpressurized volume of fluid in the aorta equal to 185 mL. The modulus of elasticity for the silicone rubber was approximately 1.3 MPa. The second aorta was an actual aorta harvested from a 1 year-old Holstein heifer. This aorta was 51 cm in length and had an inside diameter that transitioned linearly from 2.9 cm to 1.1 cm. The unpressurized volume of the aorta was 175 mL.

The experiments were designed to capture data that would be used for two purposes: (1) to compare the compliance results of equation (11) (from the blood pressure embodiment) and equation (40) (from the PWV embodiment); and (2) to demonstrate the dependency of these results on the mean arterial pressure. In order to conduct these experiments, the stroke volume of the pulsatile pump $\Delta V$ was set to 50 mL for the rubber tube and 70 mL for the Holstein aorta, the heartbeat period T was set to 1 second, and the ejection period $T_e$ was set to ⅓ second. Sixteen different needle-valve settings were used to create a range of mean pressures in the aorta between 50 and 200 mm-Hg. Each needle-valve setting corresponded to an increase in the mean arterial pressure of approximately 10 mm-Hg. Three seconds of data were taken for each experiment at a sample rate of 5 kHz.

During the experiments, the systolic and diastolic pressures in the aorta were identified and the mean arterial pressure was calculated using equation (8). Using these blood-pressure measurements with the known flow parameters of the pulsatile pump, the compliance of the aorta was calculated using equation (11). Similarly, the pressures $P_1$ and $P_2$ were taken and compared to determine the transit time $\Delta t$ between the two pressure-wave forms. The method used to calculate the transit time is known as the tangent-intersection, foot-to-foot method and is recommended for most PWV transit time measurements. Once the transit time was determined, the PWV was calculated using the standard method (PWV=L/$\Delta t$) and the compliance of the aorta was calculated using equation (40).

Figure 4:
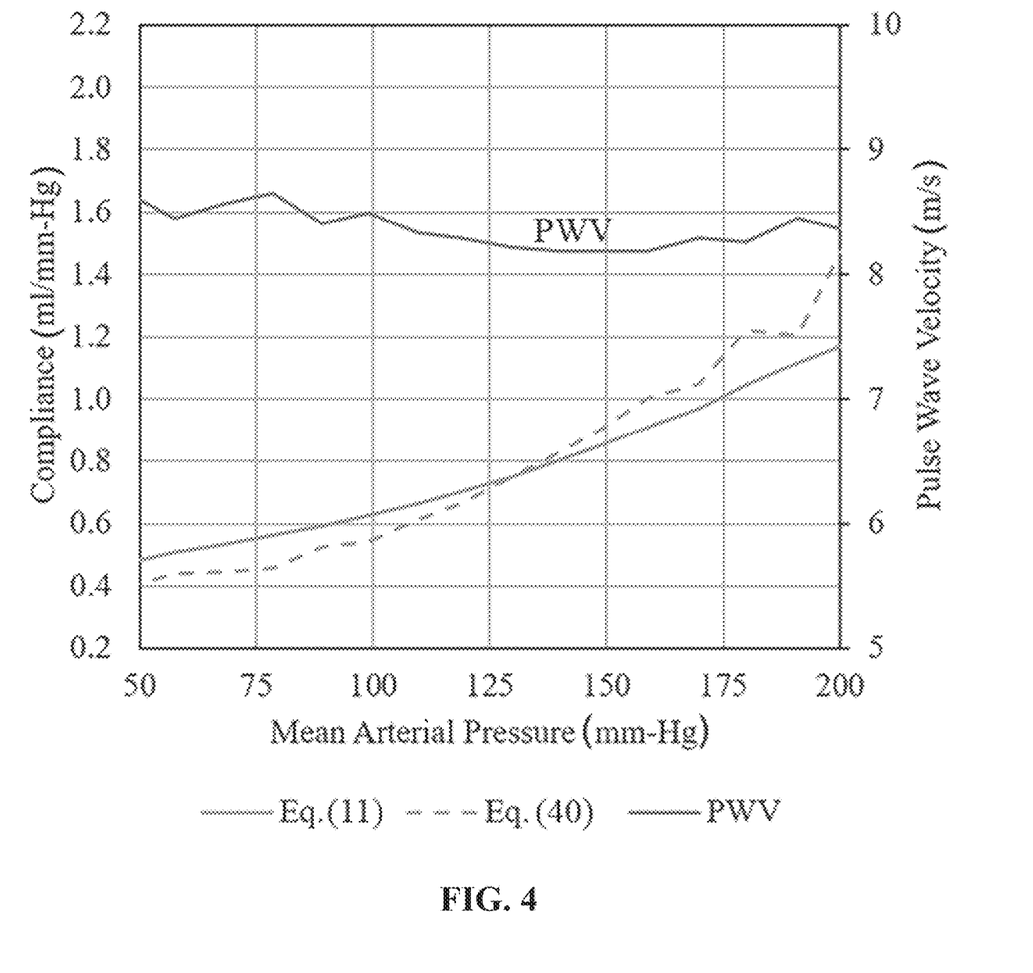
FIG. 4 is a plot showing the compliance and PWV results versus the mean arterial pressure for an elastic tube.
Figure 5:
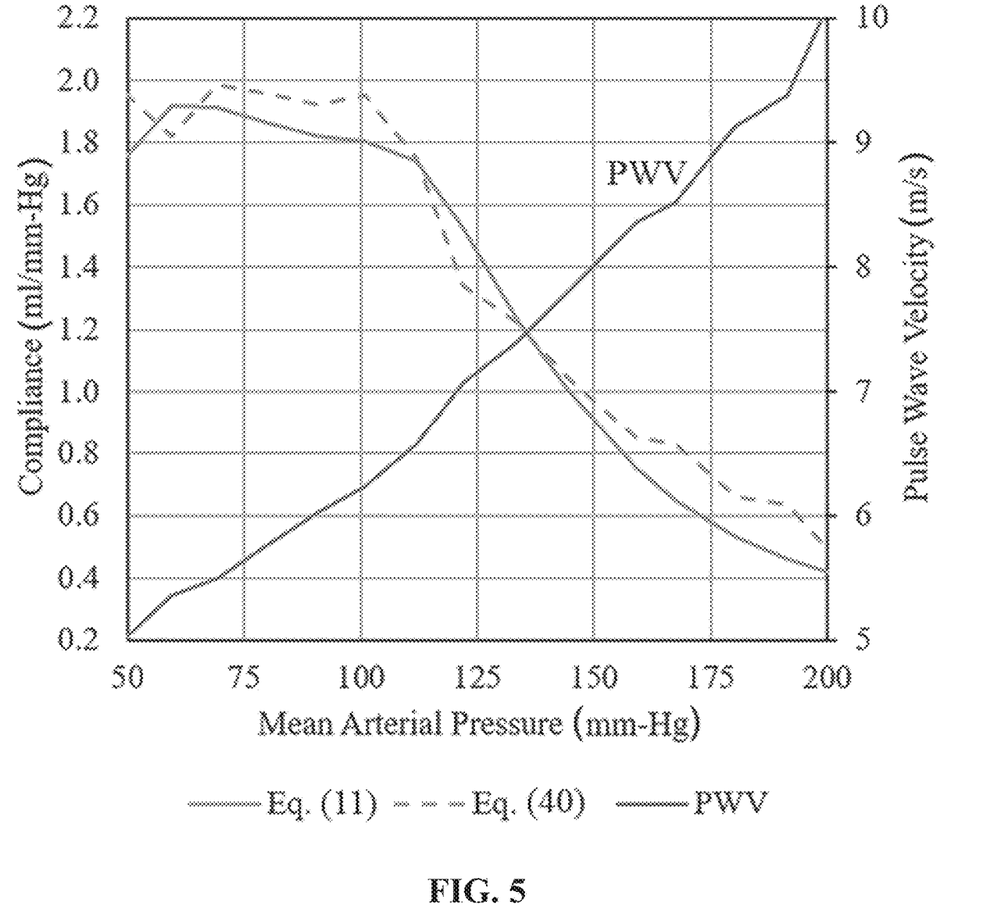
FIG. 5 is a plot showing the compliance and PWV results versus the mean arterial pressure for a Holstein aorta.

FIGS. 4 and 5 are plots showing the compliance and PWV results versus the mean arterial pressure for the elastic tube and the Holstein aorta, respectively. The scales for these two plots are identical in order to facilitate a visual comparison between them.

First, it can be observed from FIGS. 4 and 5 that the compliance results computed using equations (11) and (40), respectively, are similar in both magnitude and shape. The average percent difference between the two calculations is less than 7%. This agreement suggests that both methods may be used to compute the aortic compliance depending upon the available data. It is also shown in FIGS. 4 and 5 that the elastic tube was generally less compliant than the Holstein aorta. This difference was due to material and geometric properties of the aortae.

Second, it can be observed from FIGS. 4 and 5 that the elastic tube and the Holstein aorta present a compliance that is dependent upon the mean arterial pressure. In previous research where the aortic compliance has been described as a function of PWV, this dependence has been neglected; however, FIGS. 4 and 5 show that the mean arterial pressure must be considered when determining compliance.

Third, it can be observed from FIGS. 4 and 5 that the compliance of the rubber material increases throughout the pressure range studied in this research, and the compliance of the biological material decreases after the mean pressure exceeds 100 mm-Hg. A physical explanation for the difference in behavior is undoubtedly due to different material properties for the aortae. For example, mechanical testing has shown that the modulus of elasticity of silicon-rubber decreases slightly with strain, while the modulus of elasticity of a porcine aorta increases significantly with strain.

Of course, it should be understood that the results of the in vitro experiments described above do not have a one-to-one correspondence with the in vivo compliance that may be expected from an animal or human being. The surrounding tissues of the body and extended blood vessels will undoubtedly affect the total compliance of the cardiovascular system.

IV. Clinical Implications and Computing System

One clinical implication of the invention is that equations (11) and (12) may be used to noninvasively determine the aortic compliance and peripheral resistance of a patient if the following data is known: the diastolic pressure, the systolic pressure, the heartbeat period, the stroke volume, and the ejection period of the patient. Blood pressure is routinely measured in the clinic to determine the systolic and diastolic pressures of the blood-pressure pulse. Any suitable device may be used to measure blood pressure, such as mercury sphygmomanometers, aneroid sphygmomanometers, and digital meters. The heartbeat period (i.e., heart rate) is also routinely measured in the clinic, either manually or using any suitable heart rate monitor. The stroke volume and ejection period may be determined from echocardiogram data in order to obtain accurate numbers for a specific patient. Because an echocardiogram is more common and easier to perform than a PWV test, and since insurance companies typically pay for echocardiograms, this clinical implementation may become a standard clinical practice (possibly displacing the need for the PWV test altogether) and will provide important information that is currently not available to the physician. It is believed that access to such information will improve the prescribed treatment for patients with cardiovascular disease.

Alternatively, equations (13) and (14) may be used to noninvasively determine the aortic compliance and peripheral resistance of a patient if the following data is known: the diastolic pressure, the systolic pressure, the heartbeat period, the an estimated stroke volume. This alternative may be used when an echocardiogram is not performed and, thus, the ejection period of the patient is not known. The stroke volume may be estimated, for example, based on based on a person's age, height, medical history, weight, and/or previous measurements.

Another clinical implication of the invention is that equation (40) may be used to noninvasively determine the aortic compliance of a patient based on the PWV and mean arterial pressure (noting that the mean arterial pressure is not typically considered in connection with a conventional PWV test). The PWV may be measured using known methods for obtaining the carotid-femoral PWV measurement. The mean arterial pressure may be determined using equation (8) if the following four parameters are known—diastolic pressure, systolic pressure, heartbeat period, and ejection period (which may be obtained in the same manner as described above). Alternatively, the mean arterial pressure may be estimated using equation (9) if only the diastolic and systolic pressures are known.

Each of the above methods may be implemented using a software application executed on a computing device by performing the following steps: receiving the relevant parameters and/or test results (which will vary depending on which method is used); determining the aortic compliance and/or peripheral resistance based on the received data; and presenting the aortic compliance and/or peripheral resistance via a user interface to enable a physician or other clinician to identify a cardiovascular disease of the patient. One skilled in the art will appreciate that a number of different system configurations may be used, including a system in which the software application is executed locally on a computer located at a clinic, or, a system in which the software application is executed on a server in communication with one or more client computers located at a clinic. The latter system may be used, for example, when the software application is implemented as part of a health record system that maintains electronic medical records (EMRs) for patients.

Figure 6:
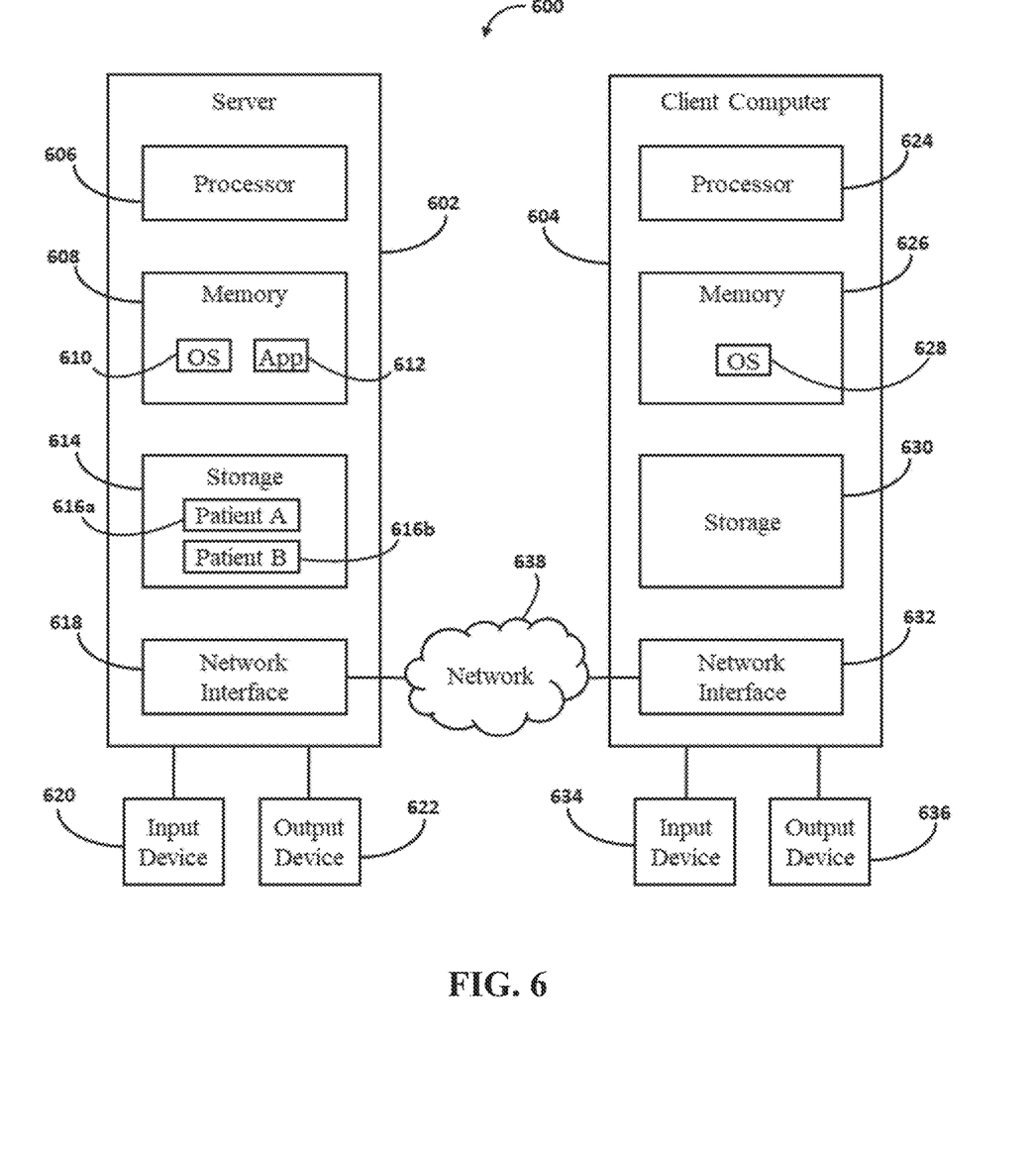
FIG. 6 is a block diagram of a computer system that may be used to implement the methods for determining aortic compliance and/or peripheral resistance in accordance with various embodiments of the invention.

Referring to FIG. 6, an exemplary embodiment of a health record system is shown generally as reference numeral 600. The system 600 includes a server 602 in communication with a plurality of client computers (wherein only one client computer 604 is shown) via a communications network 638. Each of the client computers may comprise a computer workstation, a personal computer, a laptop computer, a personal computing tablet, a smartphone, or any other electronic computing device known in the art. In general, each client computer is utilized by a user of system 600 and, accordingly, system 600 may include hundreds or even thousands of client computers.

The communications network 638 may comprise any network capable of facilitating the exchange of data between the server 602 and each client computer 604, such as those that operate according to the IEEE 802.3 protocol (e.g., Ethernet) or the IEEE 802.11 protocol (e.g., Wi-Fi). For example, in some embodiments, the communications network 638 comprises a local area network (LAN), wireless LAN (WLAN), wide area network (WAN), and/or wireless WAN (WWAN), which is connectable to other communications networks and/or portions of the Internet or an intranet. The communications infrastructure may comprise any medium that allows data to be physically transferred through serial or parallel communication channels (e.g., Ethernet cable, wireless communication channels, cellular communications, optical fiber, copper wire, etc.).

As shown in FIG. 6, the server 602 generally includes a processor 606, a memory 608, a storage device 614, a network interface 618, an input device 620, and an output device 622, all of which are connected via any suitable bus arrangement. The processor 606 may comprise a single central processing unit (CPU), multiple CPUs, a single CPU having multiple processing cores, and the like. The memory 608 may be a random access memory (RAM), for example, although other types of memory may be used. The memory stores the operating system 610 for server 602, as well as a software application 612 (described below). The storage device 614 may comprise any type of fixed and/or removable storage device suitable for storing a database containing a plurality of electronic medical records (EMRs). Two EMRs are shown in FIG. 6—an EMR for patient A 616a and an EMR for patient B 616b—although a large number of EMRs would typically be stored in storage device 614. The network interface 618 may be any type of network interface that allows the server 602 to communicate with other computers via the communications network 638. The input device 620 may be any device capable of providing input to the server 602, such as a keyboard and/or a mouse. The output device 622 may be any device capable of providing output to a user of the server 602, such as any conventional display screen.

Software application 612 is programmed to determine the aortic compliance and/or peripheral resistance of a patient by implementing any of the methods described herein. In this embodiment, the software application 612 comprises instructions that, when executed by the processor 606, cause the processor 606 to: (i) access an electronic medical record (e.g., one of EMRs 616a and 616b) to retrieve the required patient data (e.g., one or more of the diastolic pressure, the systolic pressure, the heartbeat period, the stroke volume, and the ejection period for the patient); (ii) determine the aortic compliance and/or peripheral resistance for the patient based on the retrieved patient data; and (iii) cause the aortic compliance and/or peripheral resistance to be presented on output device 636 of client computer 604 to enable identification of a cardiovascular disease of the patient.

Each client computer 604 contains a processor 624, a memory 626 (with operating system 628), a storage device 630, a network interface 632, an input device 634, and an output device 636. The description and functionality of these components is generally the same as the corresponding components described above in reference to server 602. It should be understood that the input device 634 enables a user to input patient data that is stored within a patient's EMR, i.e., the inputted patient data is transmitted from the client computer 604 to the server 602 for storage within the appropriate EMR of storage device 614. For example, the inputted data may comprise the diastolic pressure, the systolic pressure, the heartbeat period, the stroke volume, and/or the ejection period for the patient. Also, the output device 636 presents the aortic compliance and/or peripheral resistance to thereby enable a physician or other clinician to identify a cardiovascular disease of a patient. For example, the processor 606 of server 602 executes the software application 612 to determine the aortic compliance and/or peripheral resistance, as described above, and such information is transmitted from the server 602 to the client computer 604 for display on the output device 636.

It should be understood that the system 600 shown in FIG. 6 is an exemplary embodiment and that other system configurations may be used to implement the invention. For example, although system 600 includes a single server 102, any number of servers may be used for providing the functionality described herein. Also, while system 600 includes a single storage device 614 for storing patient data, the patient data may alternatively be stored in different storage devices residing on the same or different servers. For example, all or a portion of the patient data may be stored on a remote file server that is accessed through the communications network 638.

V. Conclusions

As described above, aortic compliance is known to be an independent predictor of cardiovascular morbidity and mortality. Assuming that the human aorta behaves similar to that of the Holstein heifer used in the experiments described above, it can be shown that aortic stiffening accompanies hypertension as the mean arterial blood pressure increases. This is due to the elastic properties of the biological material that is different from the silicone-rubber material used in the experiments. Thus, the following conclusions are supported by this disclosure:

(1) The aortic compliance computed from the blood pressure model (equation 11) and the PWV model (equation (40)) produce similar results, which suggests that either model may be used to compute aortic compliance based upon the available data.

(2) If a patient is able to receive echocardiograms, equation (11) may be used to regularly assess the total cardiovascular compliance for patients with cardiovascular disease.

(3) The aortic compliance is dependent upon the mean arterial pressure for both the rubber tube and the Holstein aorta, as shown in FIGS. 4 and 5. This pressure dependency has been neglected in previous models that have sought to relate PWV to aortic compliance. The correct PWV model is presented in equation (40).

(4) The differences in material properties between the rubber tube and the Holstein aorta produce different behaviors for the aortic compliance as a function of mean arterial pressure. For the rubber tube, the aortic compliance increases throughout the entire pressure range as the mean arterial pressure increases. For the Holstein aorta, the aortic compliance remains constant until the mean arterial pressure exceeds 100 mm-Hg. For pressures greater than 100 mm-Hg, the compliance of the Holstein aorta decreases markedly. This difference is due to the difference in the material properties of each aorta.

Of course, other conclusions will be readily apparent to one skilled in the art from the disclosure provided herein, or may be learned from the practice of the invention.

While the present invention has been described and illustrated hereinabove with reference to various exemplary embodiments, it should be understood that various modifications could be made to these embodiments without departing from the scope of the invention. Therefore, the present invention is not to be limited to the specific systems or methodologies of the exemplary embodiments, except insofar as such limitations are included in the following claims.

What is claimed and desired to be secured by Letters Patent is as follows:

1. A method for identifying a cardiovascular disease of a patient, comprising:
    measuring a diastolic pressure for the patient;
    measuring a systolic pressure for the patient;
    measuring a heartbeat period for the patient;
    measuring a stroke volume for the patient;
    measuring an ejection period for the patient; and
    determining a peripheral resistance for the patient based on the following equation:

$$R = \frac{P_d T_e}{\Delta V} \frac{1 - (P_s/P_d)^{\frac{T}{T-T_e}}}{1 - (P_s/P_d)^{\frac{T_e}{T-T_e}}}$$

where $P_d$ is the diastolic pressure, $P_s$ is the systolic pressure, T is the heartbeat period, $\Delta V$ is the stroke volume, and $T_e$ is the ejection period.

2. The method of claim 1, wherein the diastolic pressure, the systolic pressure, and the heartbeat period are each measured directly from the patient.

3. The method of claim 1, further comprising determining an aortic compliance for the patient based on the diastolic pressure, the systolic pressure, the heartbeat period, the stroke volume, and the ejection period.

4. A method for identifying a cardiovascular disease of a patient, comprising:
    measuring a diastolic pressure for the patient;
    measuring a systolic pressure for the patient;
    measuring a heartbeat period for the patient;
    measuring determining an estimate of a stroke volume for the patient; and
    determining a peripheral resistance for the patient based on the following equation:

$$R = \frac{P_s + P_d + \sqrt{P_s P_d}}{3} \frac{T}{\Delta V}$$

where $P_d$ is the diastolic pressure, $P_s$ is the systolic pressure, T is the heartbeat period, and $\Delta V$ is the stroke volume.

5. The method of claim 4, wherein the diastolic pressure, the systolic pressure, and the heartbeat period are each measured directly from the patient.

6. The method of claim 4, further comprising determining an aortic compliance for the patient based on the diastolic pressure, the systolic pressure, and the stroke volume.

7. A method for identifying a cardiovascular disease of a patient, comprising:
- measuring a diastolic pressure, a systolic pressure, a heartbeat period, a stroke volume, and an ejection period for the patient;
- using a computing device to:
- determine a peripheral resistance for the patient based on the following equation:

$$R = \frac{P_d T_e}{\Delta V} \frac{1 - (P_s/P_d)^{\frac{T}{T-T_e}}}{1 - (P_s/P_d)^{\frac{T_e}{T-T_e}}}$$

where $P_d$ is the diastolic pressure, $P_s$ is the systolic pressure, T is the heartbeat period, $\Delta V$ is the stroke volume, and $T_e$ is the ejection period; and
- cause the peripheral resistance to be presented via a user interface to enable identification of the cardiovascular disease of the patient.

8. The method of claim 7, wherein the computing device is further used to determine an aortic compliance for the patient based on the diastolic pressure, the systolic pressure, the heartbeat period, the stroke volume, and the ejection period.

9. A method for identifying a cardiovascular disease of a patient, comprising:
- measuring a diastolic pressure, a systolic pressure, a heartbeat period, and a stroke volume for the patient;
- using a computing device to:
- determine a peripheral resistance for the patient based on the following equation:

$$R = \frac{P_s + P_d + \sqrt{P_s P_d}}{3} \frac{T}{\Delta V}$$

where $P_d$ is the diastolic pressure, $P_s$ is the systolic pressure, T is the heartbeat period, and $\Delta V$ is the stroke volume; and
- cause the peripheral resistance to be presented via a user interface to enable identification of the cardiovascular disease of the patient.

10. The non-transitory computer readable medium of claim 9, wherein the computing device is further used to determine an aortic compliance for the patient based on the diastolic pressure, the systolic pressure, the stroke volume, and the ejection period.

* * * * *